(12) United States Patent
Karlsson et al.

(10) Patent No.: US 6,520,343 B2
(45) Date of Patent: Feb. 18, 2003

(54) FILTERING DEVICE

(75) Inventors: Håkan Karlsson, Åkersberga (SE); Per-Ivar Fransson, Åkersberga (SE)

(73) Assignee: Fibertracker AB, Akersberga (SE)

( * ) Notice: Subject to any disclaimer, the term of this patent is extended or adjusted under 35 U.S.C. 154(b) by 0 days.

(21) Appl. No.: 09/745,612

(22) Filed: Dec. 22, 2000

(65) Prior Publication Data

US 2002/0079264 A1 Jun. 27, 2002

(51) Int. Cl.[7] .............................. G01N 1/20; G01N 1/10; G01N 1/00; B01D 35/02; B01D 29/68
(52) U.S. Cl. ..................... 210/409; 210/411; 73/863.54; 73/863.81; 73/863.82; 73/863.84; 73/863.85; 73/863.86
(58) Field of Search ................................ 210/409, 411; 73/863.54, 863.81, 863.82, 863.83, 863.84, 863.85, 863.86

(56) References Cited

U.S. PATENT DOCUMENTS 3,511,374 A * 5/1970 Beal
4,297,209 A * 10/1981 De Visser et al.
4,308,142 A * 12/1981 Braukmann et al.
4,636,306 A * 1/1987 Radmall
5,176,829 A * 1/1993 Drori
5,589,080 A * 12/1996 Cho et al.
5,625,157 A * 4/1997 Piirinen et al.
5,641,894 A * 6/1997 Hosokawa

FOREIGN PATENT DOCUMENTS

WO          99/30796     *  6/1999

* cited by examiner

Primary Examiner—Thomas M. Lithgow
(74) Attorney, Agent, or Firm—Jenkens & Gilchrist, P.C.

(57) ABSTRACT

The present invention relates to a filtering device for preventing passing and blocking of unwanted particles in a suspension, which filtering device comprises an inlet and an outlet and a defined space between the inlet and the outlet, wherein the device comprises a filter means arranged in the outlet, that the filter means is arranged with openings, that the size of the openings permit particles of a size smaller than the openings to pass through, and at least one nozzle connected to a pressurised liquid source, capable of delivering a liquid jet, and arranged adjacent said outlet, wherein the said at least one nozzle is arranged such and directed such that particles that engage said filter means are removed therefrom by the liquid jet.

8 Claims, 4 Drawing Sheets

FILTERING DEVICE

TECHNICAL FIELD

The present invention relates to a filtering device and in particular a filtering device in connection with a sampler for a fiber suspension sampler.

BACKGROUND OF THE INVENTION

In the paper and cellulose industry and its processes there is a need for continuously monitoring the process regarding the wood fibers and their quality and appearance, such as length, curvature, and the like.

Often are devices used, which take samples of a certain defined volume directly from an ongoing process, such as from a process pipe with floating fiber suspension. Many of the types of devices comprise an elongated body, which is moved into the suspension whereby the end of the elongated body is provided with a compartment, into which the suspension sample enters. The elongated body is then withdrawn until the sample compartment is positioned in a chamber of the device. The chamber is connected to an inlet for liquid and an outlet out of which the sample is transported by the incoming liquid. The sample together with the liquid is then fed to an analysing equipment where the suspension is tested. Examples of such devices are disclosed in for example patent documents U.S. Pat. No. 4,147,062 and WO 99/42806.

If the sample contains particles with a rather large size, larger than expected, or the suspension is rather thick, ie a rather high fiber content in the suspension, there is a risk that either the particles will block the outlet so that not all of the sample is fed to the analysing equipment, or that the fibers will either lock the outlet due to the thickness or not all of the sample is dissolved.

One solution is then to have rather large outlet passages so as to avoid blocking of the outlet. One problem is then that larger particles, that usually are not fibers, are fed to the analysing equipment. These may disturb the testing, or worse, damage the equipment. Further, large parts of fibers are also not wanted since they affect the testing, in particular when the appearance of the fibers are to be monitored.

BRIEF DESCRIPTION OF THE INVENTION

The object of the present invention is to ascertain that the samples taken from a flow of suspension is treated and fed to the analysing device in a manner that the complete sample is available and that the sampling device is not blocked by either larger particles or fiber.

The object is achieved according to one aspect of the invention by a filtering device for preventing passing and blocking of unwanted particles in a suspension, which filtering device comprises an inlet and an outlet and a defined space between the inlet and the outlet, wherein the device comprises a filter means arranged in the outlet, that the filter means is arranged with openings, that the size of the openings of a size smaller than the openings to pass through, and at least one nozzle connected to a pressurised liquid source, capable of delivering a liquid jet, and arranged adjacent said outlet, wherein the said at least one nozzle is arranged such and directed such that particles that engage said filter means are removed therefrom by the liquid jet.

According to another aspect of the invention, the at least one nozzle is directed such that a swirling effect also is obtained in the defined space by the liquid jet.

According to a further aspect of the invention, the said filter means is the outlet opening, and that the said liquid jet from the said at least one nozzle is directed through the outlet opening and towards the defined space.

In another embodiment of the invention, the said filter means comprises a mesh arranged in said outlet opening, and that the said liquid jet from the said at least one nozzle is directed through the outlet opening and towards the defined space.

According to the invention the said at least one nozzle may be arranged and directed in a plurality of ways in order to prevent blocking of unwanted particles at the filter means.

The filtering device according to the invention may further comprise nozzles that are arranged and directed such in the defined space as to enhance the swirling effect in the defined space.

With the filtering device according to the invention any larger objects are effectively prevented from passing from the sample chamber to the measuring device, thereby preventing any objects from disturbing the measurement or even damaging the measuring equipment. The size of the outlet opening is chosen such that particles above a certain size are effectively prevented from passing. At the same time, the liquid jet from the nozzle prevents the unwanted particles from blocking the outlet opening.

The additional advantage with the liquid jet is that it causes a swirling effect inside the defined space. The swirling effect has the function of diluting the suspension and also in dissolving the suspension, which may be particularly important when dealing with rather thick pulp suspensions. In that context further liquid jet nozzles may be used, which are arranged and directed such that the jet affects the suspension and not necessarily adjacent the outlet opening.

These and other aspects of the present invention and further advantages with it will become apparent from the following detailed description of the invention and from the accompanying drawings.

BRIEF DESCRIPTION OF THE DRAWINGS

In the following description of the present invention, reference will be made to the accompanying drawings, of which.

DETAILED DESCRIPTION OF THE INVENTION

Figure 1:
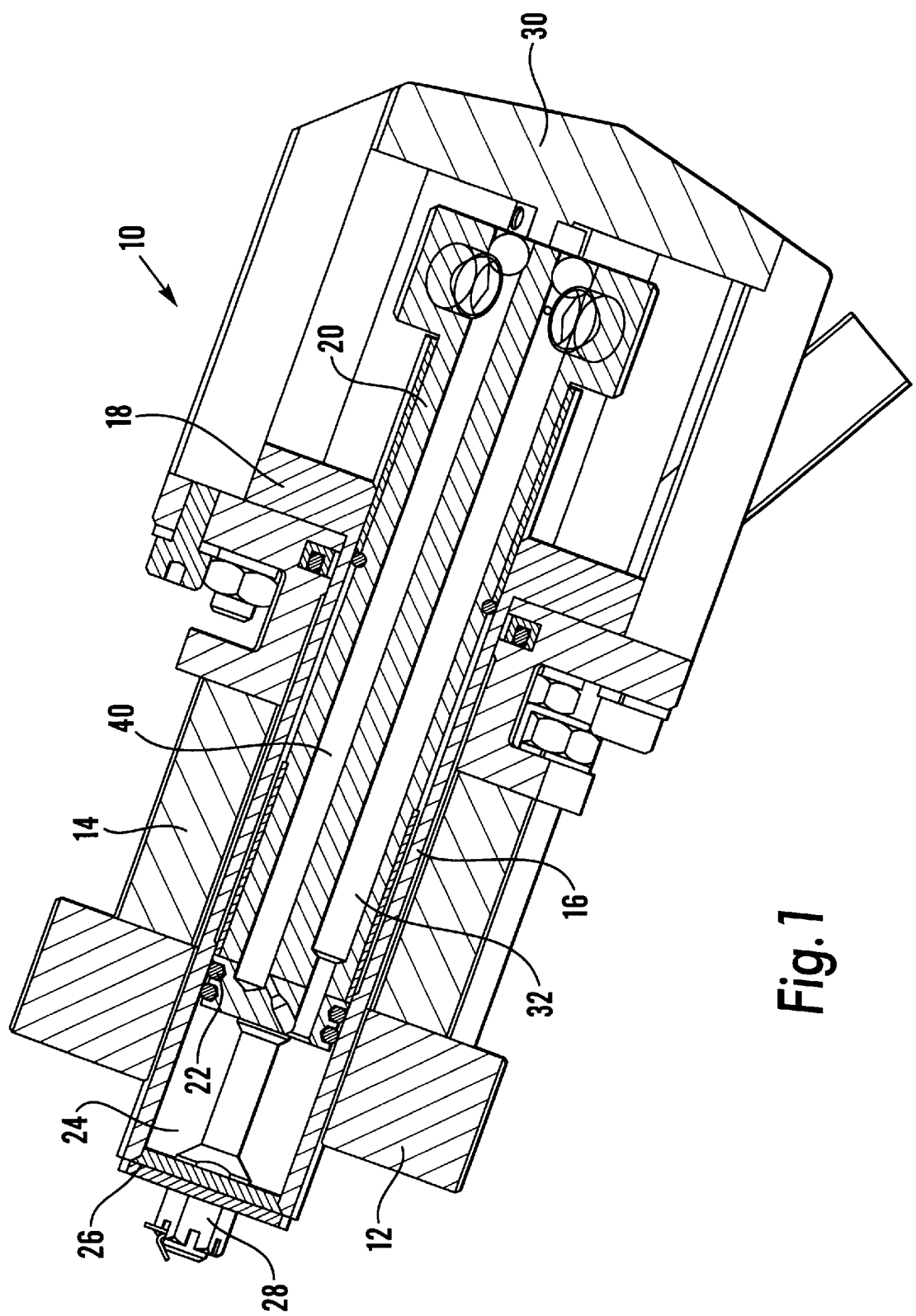
FIG. 1 shows a cross sectional view of a sampling unit, in which the present invention is comprised.

FIG. 1 shows a cross-sectional view of a sampling unit generally designated with reference numeral 10. The sampling unit is releasibly attached to the wall of a pipe 12 or the like. Inside the pipe, the material to be sampled flows, often under high pressure. The sampling unit is attached to the wall via a ball valve 14.

The sampling unit comprises an elongated tube 16 with one end protruding somewhat into the pipe. The other end of the tube is arranged with a flange 18. Inside the tube an elongated piston 20 is arranged. The end of the piston facing the pipe is arranged with a number of seals 22. The end of the piston is arranged with a sampling chamber 24 formed as a compartment with a sideways directed opening. The end of the sampling chamber is arranged with a lid 26, held in place with a nut 28, where the outer circumference of the lid abuts the end surface of the tube.

Figure 2:
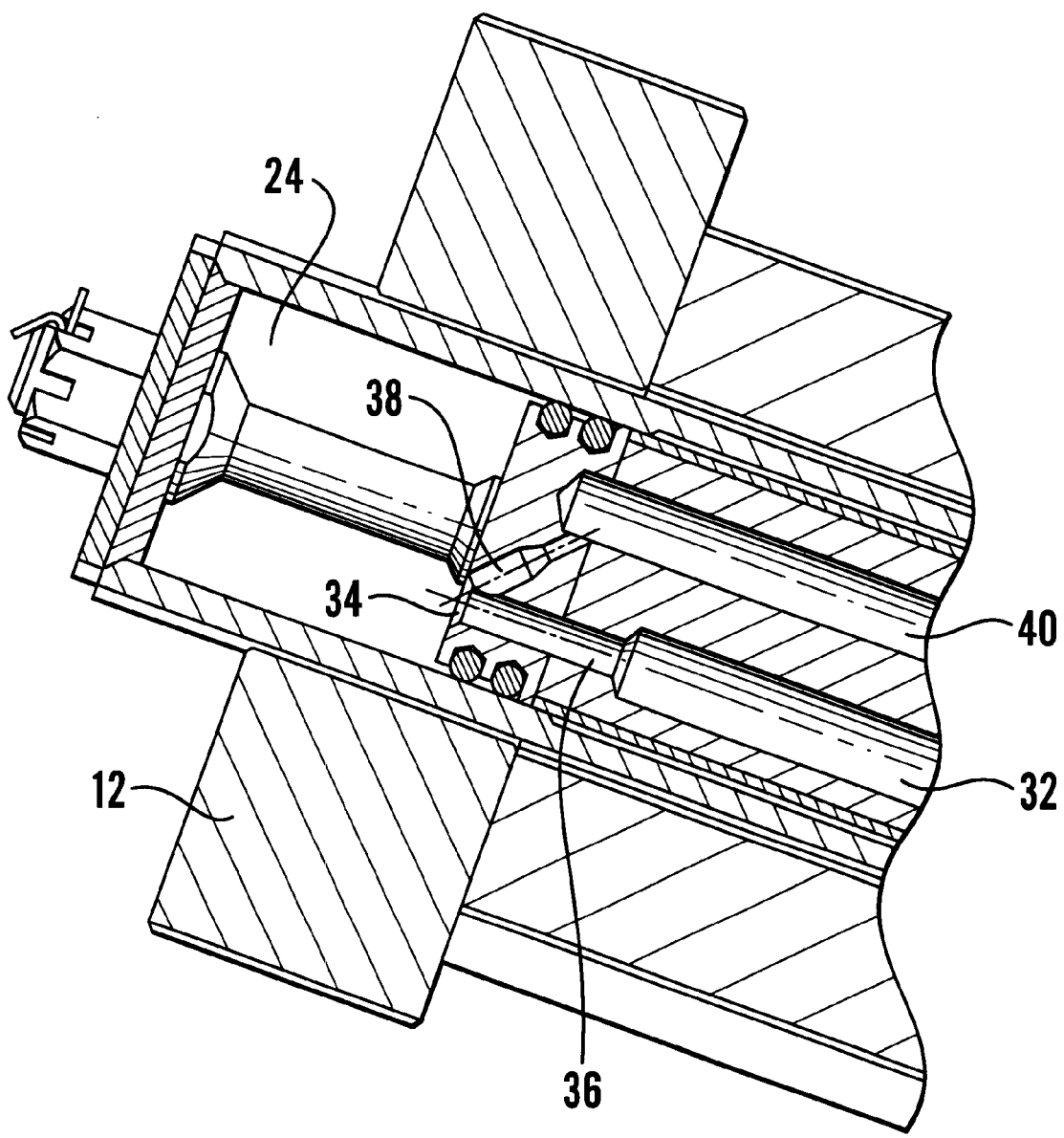
FIG. 2 shows a detailed view of the sampling chamber of FIG. 1, with a one embodiment of the present invention.

The opposite end of the piston is connected to an actuator 30 capable of moving the piston reciprocally when activated. An outlet passage 32 is arranged from the sampling chamber and through the piston, and from the piston via flexible conduits to a measuring device (not shown). The outlet passage comprises an outlet opening 34, a passage 36 with a first predetermined diameter, chosen in relation to the maximum allowable particle size to pass through, and thereafter a second, larger diameter passage 32. A liquid injection nozzle 38 is arranged adjacent the opening 34 of the outlet passage, FIG. 2. The injection nozzle 38 is arranged inclined in respect to the longitudinal axis of the outlet passage, whereby the point of intersection between the longitudinal axis of the outlet passage and the longitudinal axis of the nozzle is arranged in the sample chamber just outside the opening 34. The liquid injection nozzle is connected to a passage 40 through the piston and further to a pressurised liquid source (not shown) via flexible conduits.

The function of the sampling unit and the present invention is as follows. When a sample of for example a pulp suspension is to be taken, the actuator 30 is activated, whereby the piston 20 with the sampling chamber is pushed into the pipe. A part of the suspension passing through the pipe is forced into the sampling chamber 24. The actuator then draws the piston and the sampling chamber back, whereby the lid 26 closes against the end of the pipe. Pressurised liquid is then fed through the passage 40 and the injection nozzle 38 into the sampling chamber as a liquid jet. The injected liquid will on the one hand cause a swirling action in the sampling chamber and on the other hand dilute the suspension. Diluted pulp will flow through the outlet opening 34 and further through the outlet passage 32. Because of the arrangement of the nozzle in relation to the opening, the effective passage for the suspension will be somewhat smaller than the outlet opening. The pulp is then fed to a measuring device for analysis of the collected pulp. Particles that are larger than the outlet passage are thus prevented from passing through and will remain in the sampling chamber. These particles will be dispensed of in the subsequent sampling cycle. The injection jet will further prevent the larger particles from blocking the outlet opening because it is directed at the outlet opening.

The injection jet should have such a velocity or force that it is capable of moving the larger particles from the outlet opening. Further, the injection jet should be rather concentrated so that the diluted pulp is not prevented by the jet from entering the outlet opening.

The injection jet also has the advantage of dissolving rather thick pulp suspensions sampled, which otherwise might not be completely dissolved and diluted. If not so, the whole sample is not fed to measuring unit. It might further be so that if the sample is not dissolved completely, the next sample is not a completely new sample, and further that there is a risk of build-up of pulp in the sample chamber, which ultimately may block it. In this context it is rather important that the injection jet through its force and the swirling action is capable of dissolving the whole sample collected in the sampling chamber.

Figure 3:
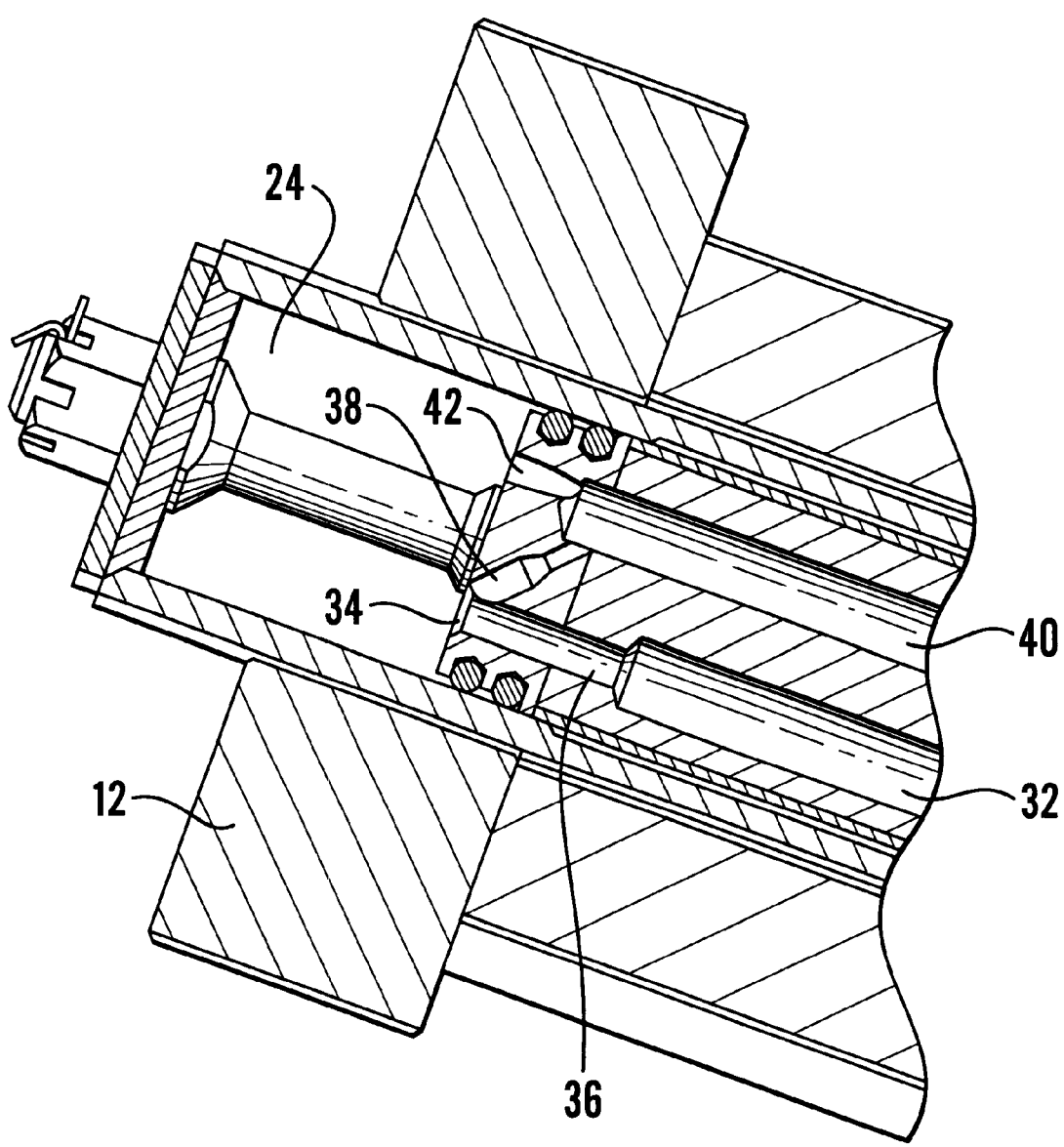
FIG. 3 shows a variant of the detailed view of FIG. 2.

It is conceivable to have more than one injection nozzle to increase the swirling effect. FIG. 3 shows a second injection nozzle 42 directed towards the interior of the sampling chamber, the purpose of which is to increase the swirling and dissolving effect.

Figure 4:
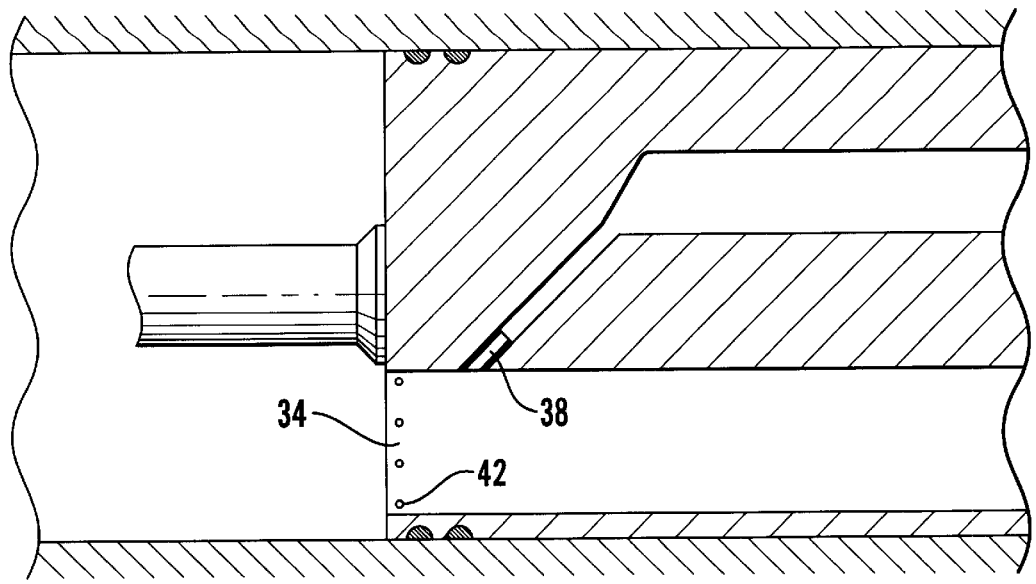
FIG. 4 shows a detailed view of the sampling chamber of FIG. 1 with a second embodiment of the present invention.

FIG. 4 shows another embodiment of the present invention wherein the outlet opening 34 is chosen larger than the largest admissible particles. For preventing the larger particles from passing, the outlet opening is arranged with a mesh 42. The mesh effectively prevents these larger particles from passing at the same time as the injection jet from the nozzle prevents them from blocking the outlet opening. The advantage with a larger outlet opening is that a larger outlet flow may be obtained. Because of the larger opening there is however a risk that one injection jet is not capable of preventing larger particles from blocking a part of the outlet opening. In that case it is conceivable to use more than one injection nozzle arranged in the outlet opening.

Figure 5:
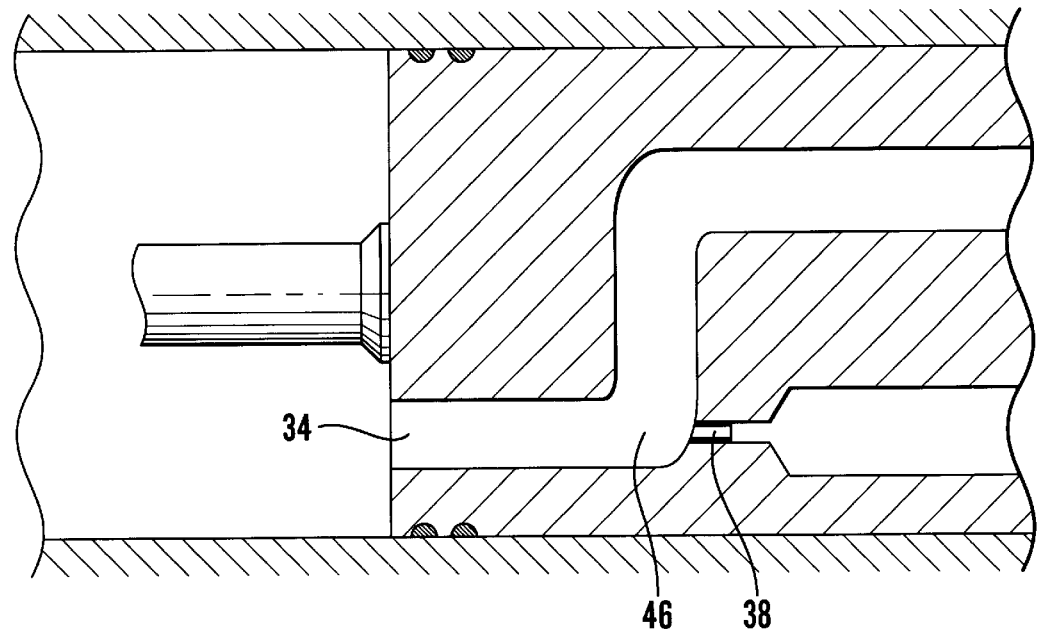
FIG. 5 shows a detailed view of the sampling chamber of FIG. 1 with a third embodiment of the present invention.

FIG. 5 shows a further variant of the invention, wherein the outlet passage after the opening is arranged with a bend or a curved portion 46, and wherein the injection nozzle is arranged in the bend and directed towards the outlet opening. This arrangement might provide a simpler solution manufacturing-wise as compared to the inclined nozzle embodiment. With this arrangement the effective passage for the suspension to pass through of the outlet passage will thus be smaller than the actual size of the outlet passage.

It is to be understood that the outlet opening may be designed in many different ways and that one or several nozzles may be used and directed in many different ways in order to obtain the desired function of the invention. It is thus to be understood that the embodiments described above and shown in the drawings are non-limiting examples of the present invention and that it may be modified within the scope of protection defined by the patent claims.

In this context it is to be understood that other types of sampling units may be utilised with the present invention for sampling and feeding to a measuring device or other collection an/or analysis station.

What is claimed is:

1. A filtering device for preventing passing and blocking of unwanted particles in a suspension, intended to be arranged in a sampling chamber constituting a defined space and comprising an inlet arranged to the sampling chamber for allowing entry of a sample of the suspension and an outlet arranged to the sampling chamber for allowing withdrawal of the sample, which filtering device comprises a filter means arranged in the outlet, that the filter means is arranged with at least one opening, that the size of the at least one opening permits particles of a size smaller than the at least one opening to pass through, and at least one nozzle connected to a pressurized liquid source, capable of delivering a liquid jet, and arranged adjacent said outlet, wherein the said at least one nozzle is arranged, directed and operable such that particles that engage said filter means are removed from the filter means by the liquid jet during withdrawal of the sample from the sample chamber.

2. The filtering device according to claim 1, wherein the at least one nozzle is directed such that a swirling effect also is obtained in the defined space by the liquid jet.

3. The filtering device according to claim 1, wherein the said filter means is an outlet opening, and that the said liquid jet from the said at least one nozzle is directed through the outlet opening and towards the defined space.

4. The filtering device according to claim 1, wherein the said filter means comprises a mesh arranged in said outlet opening, and that the said liquid jet from the said at least one nozzle is directed through the outlet opening and towards the defined space.

5. The filtering device according to claim 1, wherein the at least one nozzle is arranged with surfaces inclined with respect to the center axis to the outlet passage.

6. The filtering device according to claim 1, wherein the outlet passage is arranged with a bend after the outlet opening as seen in the flow direction, and that said at least one nozzle is arranged in said bend and directed towards said outlet opening.

7. The filtering device according to claim 1, wherein it comprises further nozzles connected to a pressurized liquid source, that said further nozzles are arranged and directed such in the defined space as to enhance the swirling effect in the defined space.

8. The filtering device according to claim 1, further comprising a sampling unit for collecting defined samples of pulp suspensions.

* * * * *